(12) United States Patent
Takubo

(10) Patent No.: US 10,172,803 B2
(45) Date of Patent: Jan. 8, 2019

(54) HARD CAPSULE FORMULATION

(71) Applicant: Capsugel Belgium NV, Bornem (BE)

(72) Inventor: Takahisa Takubo, Kanagawa (JP)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 14/771,161

(22) PCT Filed: Mar. 3, 2014

(86) PCT No.: PCT/IB2014/059408
§ 371 (c)(1),
(2) Date: Aug. 27, 2015

(87) PCT Pub. No.: WO2014/136038
PCT Pub. Date: Sep. 12, 2014

(65) Prior Publication Data
US 2016/0015651 A1    Jan. 21, 2016

(30) Foreign Application Priority Data
Mar. 7, 2013  (JP) ................. 2013-045989

(51) Int. Cl.
*A61K 9/48* (2006.01)
*A23L 33/00* (2016.01)
(Continued)

(52) U.S. Cl.
CPC ............ *A61K 9/4875* (2013.01); *A23L 33/00* (2016.08); *A23P 10/30* (2016.08); *A61K 9/4858* (2013.01);
(Continued)

(58) Field of Classification Search
None
See application file for complete search history.

(56) References Cited

U.S. PATENT DOCUMENTS 3,374,146 A * 3/1968 Blicharz ............ A61K 9/4858
                                                   424/452
3,427,378 A * 2/1969 Elowe ................ A61K 9/4866
                                                   424/456
(Continued)

FOREIGN PATENT DOCUMENTS

EP     2988734       3/2016
JP   2007-302570   11/2007
(Continued)

OTHER PUBLICATIONS

Tonnesen et al. "Alginate in Drug Delivery Systems", Drug Develpoment and Industrail Pharmacy, 28(6), 621-630 (2002).*
(Continued)

*Primary Examiner* — Isis A Ghali
(74) *Attorney, Agent, or Firm* — Klarquist Sparman, LLP

(57) ABSTRACT

A problem of the present disclosure is, in one embodiment, to create a hard capsule formulation that includes a pharmaceutical agent or the like whose components deteriorate upon contact with an acid, in which the pharmaceutical agent or the like does not deteriorate due to gastric acid penetrating into the outer shell of the hard capsule. A hard capsule formulation comprising a hard capsule with acid resistance, in which the hard capsule is not treated with enteric coating, and the hard capsule formulation comprises an agent to inhibit invasion of gastric fluid and a pharmaceutical agent in the hard capsule.

7 Claims, 9 Drawing Sheets

(51) Int. Cl.
*A61K 35/50* (2015.01)
*A61K 38/16* (2006.01)
*A61K 38/43* (2006.01)
*A61K 38/48* (2006.01)
*A23P 10/30* (2016.01)

(52) U.S. Cl.
CPC .......... *A61K 9/4866* (2013.01); *A61K 35/50* (2013.01); *A61K 38/164* (2013.01); *A61K 38/43* (2013.01); *A61K 38/482* (2013.01); *C12Y 304/21062* (2013.01)

(56) References Cited

U.S. PATENT DOCUMENTS

| | | | | |
|---|---|---|---|---|
| 4,497,158 | A * | 2/1985 | Durr | A61J 3/074 424/452 |
| 4,601,896 | A | 7/1986 | Nugent | |
| 5,849,327 | A | 12/1998 | Berliner et al. | |
| 2006/0286282 | A1* | 12/2006 | Kamaguchi | B01J 13/02 426/658 |
| 2007/0148248 | A1 | 6/2007 | Chidambaram | |
| 2008/0145355 | A1* | 6/2008 | Porubcan | A61K 9/4866 424/94.21 |
| 2010/0260857 | A1* | 10/2010 | Fallon | A61K 9/5015 424/491 |
| 2012/0288562 | A1 | 11/2012 | Cade et al. | |

FOREIGN PATENT DOCUMENTS

| | | |
|---|---|---|
| JP | 2013-505928 | 2/2013 |
| JP | 2014-172850 | 9/2014 |
| JP | 2016-510064 | 4/2016 |
| WO | WO96/17599 | 6/1996 |
| WO | WO2005/025609 | 3/2005 |
| WO | WO2006/082824 | 8/2006 |
| WO | WO2007/098612 | 9/2007 |
| WO | WO2013/067483 | 5/2013 |
| WO | WO2014/136038 | 9/2014 |

OTHER PUBLICATIONS

Tabakha "HPMC Capsules: Current status and Future Prospect", J Pharm Pharnnaceut Sci; 13 (3) 428-442. (Year: 2010).*
International Search Report and Written Opinion for PCT/IB2014/059408 (dated Apr. 23, 2014).
International Preliminary Report on Patentability for PCT/IB2014/059408, dated Sep. 8, 2015.
Office Action from European Patent Office for European Patent Application No. 14710394.9, dated Jul. 28, 2016.
Office Action from European Patent Office for European Patent Application No. 14710394.9, dated Apr. 11, 2018.
Notice of Reasons for Rejection from the Japanese Patent Office for Japanese Patent Application No. 2015-560825, dated Oct. 31, 2017.

* cited by examiner

HARD CAPSULE FORMULATION

CROSS REFERENCE TO RELATED APPLICATIONS

This is the U.S. National Stage of International Application No. PCT/IB2014/059408, filed Mar. 3, 2014, which was published in English under PCT Article 21(2), which in turn claims priority to JP 2013-045989, filed Mar. 7, 2013. The Japanese application is incorporated herein in its entirety.

TECHNICAL FIELD

The present disclosure is related to a hard capsule formulation.

BACKGROUND

As a means for delivering a pharmaceutical agent to the intestine without the agent disintegrating in the stomach, a method has been known of applying an enteric coating onto a coating film (i.e. onto the shell) of a hard capsule.

Recently, a hard capsule in which the film (outer shell film) itself of the hard capsule is acid-resistant has been developed and sold (for example, "DRCAPS™" from Capsugel). Such hard capsules are superior in that a further enteric coating does not necessarily have to be applied onto the coating film (outer shell) of the capsule.

These kinds of hard capsules having acid resistance are useful because the shell does not normally dissolve even in an acidic solution having a pH of 1.2 (in other words, because the hard capsule does not disintegrate in the stomach of a living organism). In particular, when filling a hard capsule with a substance such as a pharmaceutical agent or the like for which no problems would occur as long as the hard capsule does not disintegrate in the stomach (for example, garlic and the like which may cause a return smell), the anticipated effects can be achieved with no remarkable problems.

However, upon careful examination of hard capsule formulations, including hard capsules with acid resistance that do not achieve sufficient effects, the present inventors made the surprising discovery that even if the hard capsule does not disintegrate in the stomach, gastric acid may gradually penetrate through the hard capsule outer shell over time because the shell itself of the hard capsule is not waterproof. As a result, the present inventors discovered that, since a substance such as a pharmaceutical agent or the like that is filled within a hard capsule makes contact with an acid (gastric acid), the anticipated effects cannot be achieved when filling a hard capsule with a substance such as a pharmaceutical agent or the like (for example, proteins (royal jelly, milk proteins, etc.), enzymes (nattokinase (source *Bacillus subtilis* var.natto), coenzymes, etc.), and viable bacteria (lactic acid bacteria, bifidobacteria, etc.) whose components deteriorate (change, decompose, or die) upon contact with an acid.

WO 2007/098612 A1 relates to gelatin compositions with covalent attachments forming functionalized gelatin.

U.S. Pat. No. 5,849,327 relates to pharmaceutical compositions with polymeric beads and polysaccharides, where the dosage form has an enteric coating.

United States Patent Application, Publication No. 2012/0288562 A1 assigned to Capsugel Belgium NV relates to acid resistant capsules.

SUMMARY

Considering the above-described problems, an objective of the present disclosure is, in one embodiment, to create a hard capsule formulation that includes a pharmaceutical agent or the like whose components would deteriorate upon contact with an acid, in which the pharmaceutical agent or the like does not deteriorate due to gastric acid penetrating into the outer shell of the hard capsule.

As a result of keen examination over a long period of time, the present inventors discovered that the above-mentioned problem could be solved by developing a hard capsule formulation having the features described below.

In one embodiment, the hard capsule formulation of the present disclosure includes a hard capsule with acid resistance, in which the hard capsule is not treated with an enteric coating and the hard capsule formulation includes an agent to inhibit invasion of gastric fluid and a pharmaceutical agent in the hard capsule.

The agent to inhibit invasion of gastric fluid is an agent that contributes to substantially (completely, or partially) prevent an acidic solution (gastric fluid in a living organism) from invading into the hard capsule through the outer shell of the hard capsule and infiltrating into the materials filled within the hard capsule.

In one embodiment, the agent to inhibit invasion of gastric fluid is a gelling agent and/or a water repellent agent. In other words, both a gelling agent and a water repellent agent can also be used. These agents are believed to contribute to the inhibitory effect through different mechanisms, and using both a gelling agent and a water repellent agent is thought to be even more useful. The gelling agent is believed to contribute to preventing an acidic solution (gastric fluid in a living organism) from infiltrating into the materials filled within the hard capsule by swelling. In contrast, the water repellent agent is believed to contribute to preventing an acidic solution (gastric fluid in a living organism) from infiltrating by the water repellent action thereof.

In one embodiment of the hard capsule formulation, the gelling agent can be included as a powder. Such a gelling agent can be preferably selected from the group consisting of guar gum, pectin, ι (iota) type carrageenan, λ (lambda) type carrageenan, xanthan gum, locust bean gum, alginate, alginic acid, tamarind gum, glucomannan, agar, curdlan, gellan gum, and collagen. Such a gelling agent can be more preferably selected from the group consisting of guar gum, λ (lambda) type carrageenan, xanthan gum, and locust bean gum.

In one embodiment of the hard capsule formulation, the water repellent agent can be included as a powder. Such a water repellent agent can be preferably selected from the group consisting of calcium stearate, magnesium stearate, and carnauba wax.

In one embodiment, the hard capsule formulation includes a pharmaceutical agent. In order to most effectively utilize the technology of the hard capsule formulation of the present disclosure, a pharmaceutical agent whose components deteriorate (change/decompose/die) upon contact with an acid can be used. Such pharmaceutical agents include, for example, proteins (royal jelly, milk proteins, etc.), enzymes (nattokinase (source *Bacillus subtilis* var.natto), coenzymes, etc.), and viable bacteria (lactic acid bacteria, bifidobacteria, etc.).

In the hard capsule formulation of the present disclosure, the amount of the gelling agent and water repellent agent to be used is not particularly limited. Under given conditions (the pharmaceutical agent(s), excipient(s), hard capsule, the capacities thereof, etc.), the gelling agent and water repellent agent can be included in an amount at which the effect thereof is demonstrated at an anticipated level. For example, on a weight basis, the amount of the gelling agent and water repellent agent can be 25% or less, preferably 20% or less, more preferably 10% or less, and even more preferably 9% or less of the total weight of the materials filled within the hard capsule.

The hard capsule formulation disclosed herein can be used for any purpose as long as it is appropriate, but in particular, it can be used as a capsule for medical or health food applications.

The hard capsule to be used in the hard capsule formulation of the present disclosure can be manufactured by a method known to those skilled in the art, and a commercially available hard capsule can be also used. Any material can be used for the hard capsule, and among such materials, gelatin, hydroxypropyl methyl cellulose, and pullulan are preferable. The hard capsule can be manufactured by a method in which a molding pin is immersed into an aqueous solution (gel) in which the material of the hard capsule (and a gelling agent and/or a gelling adjuvant as desired) has been dissolved and then the molding pin is pulled out, and the hard capsule material is then gelled and dried.

Plasticizers, preservatives, dispersing agents, and other additives for improving the production of the hard capsule are known, and their appropriate use in the capsule of the present disclosure is within the scope of modifications that can be anticipated from those skilled in the art.

In one embodiment, the hard capsule formulation of the present disclosure includes a hard capsule, and an agent to inhibit invasion of gastric fluid and a pharmaceutical agent in the hard capsule. Herein, the hard capsule can be subjected to application of an enteric coating onto a coating film (i.e. an outer shell) of the hard capsule. However, in order to most effectively utilize the technology of the hard capsule formulation of the present disclosure, a hard capsule in which an enteric coating is not applied onto the outer shell of the hard capsule is preferably used. Further, in order to most effectively utilize the technology of the hard capsule formulation of the present disclosure, the hard capsule is preferably acid-resistant. Herein, acid resistance implies a property in which the hard capsule does not substantially dissolve (disintegrate) due to gastric fluid in a living organism (stomach). It is preferable that the hard capsule does not dissolve in the stomach but does dissolve in the intestine. Such a hard capsule with acid resistance is commercially available (for example, DRCAPS™ from Capsugel). In one embodiment, the agent to inhibit invasion of gastric fluid can be selected from the group consisting of guar gum, λ (lambda) type carrageenan, xanthan gum, and locust bean gum, calcium stearate, magnesium stearate, and carnauba wax.

The scope of the present disclosure also includes arbitrary combinations of one or a plurality of the features described above.

In one embodiment, a hard capsule formulation includes a pharmaceutical agent or the like whose components deteriorate upon contact with an acid in a hard capsule, in which the pharmaceutical agent or the like can be prevented from deteriorating due to gastric fluid that penetrates into the hard capsule shell.

DESCRIPTION

The terms used in the present specification are used to explain the specific embodiments described herein, and are not intended to limit the present disclosure.

The term "include" as used in the present specification is intended to mean that the matters as described (members, steps, elements, or numbers, etc.) exist except when another understanding thereof is explicit from the context, and such terms do not exclude the existence of other matters (members, steps, elements, numbers, etc.).

Unless a different definition is given, all of the terms used herein (including technical terms and scientific terms) have the same meaning as those widely understood by those skilled in the art in the technical field to which the present disclosure belongs. Unless a different definition is explicitly given, the terms used herein should be interpreted with a meaning that is consistent with the meaning in the present specification and the related technical field, and they should not be idealized or interpreted with an excessively formal meaning.

Some of the embodiments of the present disclosure may be explained referring to schematic diagrams, but the schematic diagrams may be exaggerated in order to clearly explain such embodiments.

The present disclosure will now be explained in further detail below referring to examples. However, the present disclosure can be embodied by various embodiments and should not be construed as limited to the examples described herein.

EXAMPLES

Example 1

Figure 4:
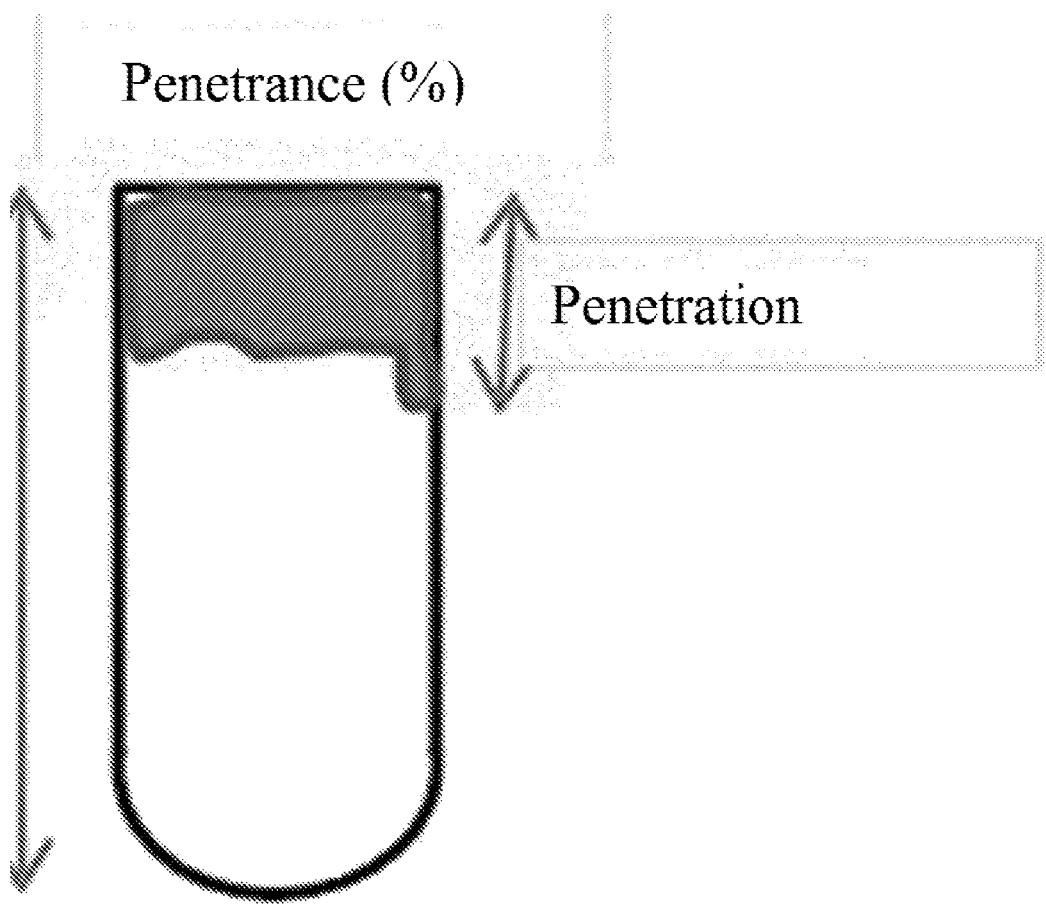
FIG. 4 is a schematic diagram of Example 1 and Example 2.

Each of the powders in Table 1, which are food additives or pharmaceutical additives, was filled without mixing with any other powder into a divided body part of an acid-resistant hard capsule from Capsugel (DRCAPS™, Size 1, colorless and transparent) up to an opening end surface of the body. Next, 100 μL of Japanese Pharmacopeia, First Solution (pH 1.2 solution) colored with Blue No. 1 was dropped thereon, and the penetrance (%) after 60 minutes was measured (refer to FIG. 4).

Penetrance is defined by the distance that the blue-colored solution penetrated relative to the body length (16.6 mm). In other words, if the blue-colored solution penetrated 4.15 mm, then the penetrance would be 25% (upon rounding up or down). If the penetrance was smaller, this means that the penetration of an acidic solution was more largely inhibited (in terms of within a living organism, it means that the penetration of gastric fluid was more largely inhibited).

In the present example, the penetrance was evaluated based on the following standards:
Excellent: 10% or less
Good: 11% or more to 20% or less
Acceptable: 21% or more to 50% or less
Unsuitable: 51% or more The powders used in the present example were gelling agents (also referred to as gelling agent powders when appropriate; gelling adjuvants were not used) and water repellent agents (also referred to as water repellent powders when appropriate). Normal excipients were used as the comparative examples.

The results are shown in Table 1.

TABLE 1

| | Test Powder | Product Name | Penetrance (%) | Evaluation |
|---|---|---|---|---|
| Gelling Agents | pectin | UNIPECTINE 400 from Unitec Foods Co., Ltd.. | 8 | Excellent |
| | pectin | UNIPECTINE 355S from Unitec Foods Co., Ltd.. | 18 | Good |
| | pectin | GENU Pectin DF-Z-J from Sansho Co., Ltd. | 10 | Excellent |
| | pectin | GENU Pectin LM-104AS-J from Sansho Co., Ltd. | 13 | Good |
| | pectin | GENU Pectin LM-104AS-FS-J from Sansho Co., Ltd. | 15 | Good |
| | pectin | GENU Pectin LM-102AS-J from Sansho Co., Ltd. | 17 | Good |
| | pectin | GENU Pectin BB rapid set-J from Sansho Co., Ltd. | 5 | Excellent |
| | pectin | GENU Pectin DD slow set-J from Sansho Co., Ltd. | 5 | Excellent |
| | xanthan gum | Inagel ASP Xanthan from Ina Food Industry, Co., Ltd. | 13 | Good |
| | xanthan gum | Echogum T/Keltrol T from DSP Gokyo Food & Chemical Co., Ltd.. | 10 | Excellent |
| | xanthan gum | Vis Top D-3000-C from San-Ei Gen F.F.I., Inc. | 12 | Good |
| | locust bean gum | Locust Bean Gum F from San-Ei Gen F.F.I., Inc. | 14 | Good |
| | locust bean gum | MEYPRO-LBGFLEURM-175 from Sansho Co., Ltd. | 15 | Good |
| | locust bean gum | GENU GUM RL-200-J from Sansho Co., Ltd. | 12 | Good |
| | tamarind gum | Glyloid 6C from DSP Gokyo Food & Chemical Co., Ltd.. | 8 | Excellent |
| | glucomannan | Rheolex RS from Shimizu Chemical Corp. | 10 | Excellent |
| | glucomannan | Propol A from Shimizu Chemical Corp. | 31 | Acceptable |
| | guar gum | KT-0104 from DSP Gokyo Food & Chemical Co., Ltd.. | 6 | Excellent |
| | curdlan | Curdlan from Takeda-Kirin Foods Corp. | 19 | Good |
| | gellan gum | Kelcogel from Sansho Co., Ltd. | 18 | Good |
| | porcine collagen | Collagel A from Gelita | 8 | Excellent |
| | κ (kappa) type carrageenan | Gelcarin GP812NF from FMC | 15 | Good |
| | ι (iota) type carrageenan | Gelcarin GP379NF from FMC | 15 | Good |
| | sodium polyacrylate | Panakayaku CP from Nippon Shokubai Co., Ltd. | 12 | Good |
| Comparative Examples | corn starch | Nisshoku Corn Starch W from San-Ei Gen F.F.I., Inc. | 56 | Unsuitable |
| | crystalline cellulose | Crystalline Cellulose FD301 from Asahi Kasei Chemicals Corp. | 53 | Unsuitable |
| Water Repellent Agents | calcium stearate | Taiyo Chemical Industry Co., Ltd. | 4 | Excellent |
| | magnesium stearate | Taiyo Chemical Industry Co., Ltd. | 2 | Excellent |
| | carnauba wax | Freund Corp. | 3 | Excellent |
| Comparative Examples | cyclodextrin | Celdex B-100 from Nihon Shokuhin Kako Co., Ltd. | 52 | Unsuitable |
| | lactose | Kanto Chemical Co., Inc. | 100 | Unsuitable |

As shown in Table 1, it is clear that penetration of the acidic solution was very remarkably inhibited when using a gelling agent or a water repellent agent compared to the comparative examples (normal excipients). The penetrance in the case of lactose, which was one comparative example, was 100%. This means that the acidic solution penetrated the entire body length (16.6 mm).

Example 2

The penetrance was measured according to the same method as in Example 1 upon mixing 10%, 25%, and 50% by weight of a certain powder (gelling agent or water repellent agent) into lactose which is popular for an excipient of a capsule (in Example 1, the penetrance in the case of lactose was 100%).

In this example, the penetrance was evaluated based on the following standards:
Rank AA: penetrance of 10% or less for a 10% mixture
Rank A: penetrance of 10% or less for a 25% mixture
Rank B: penetrance of 15% or less for a 25% mixture
Rank C: penetrance of 50% or less for a 25% mixture
Rank Unsuitable: anything other than the above
The results are shown in Table 2.

TABLE 2

| Test Powder | Product Name | % Mixed into Lactose | Penetrance (%) | Evaluation |
|---|---|---|---|---|
| pectin | UNIPECTINE 400 from Unitec Foods Co., Ltd.. | 10 | 28 | B |
| | | 25 | 11 | |
| | | 50 | 12 | |
| pectin | UTFC LM QS 400C from Unitec Foods Co., Ltd.. | 10 | 29 | B |
| | | 25 | 13 | |
| | | 50 | 11 | |
| pectin | GENU Pectin BB rapid set-J from Sansho Co., Ltd. | 10 | 12 | A |
| | | 25 | 9 | |
| | | 50 | 7 | |
| pectin | GENU Pectin DD slow set-J from Sansho Co., Ltd. | 10 | 10 | AA |
| | | 25 | 7 | |
| | | 50 | 8 | |
| xanthan gum | Echogum T/Keltrol T from DSP Gokyo Food & Chemical Co., Ltd.. | 10 | 19 | A |
| | | 25 | 6 | |
| | | 50 | 6 | |
| xanthan gum | Vis Top D-3000-C from San-Ei Gen F.F.I., Inc. | 10 | 23 | A |
| | | 25 | 8 | |
| | | 50 | 7 | |
| locust bean gum | GENU GUM RL-200-J from Sansho Co., Ltd. | 10 | 25 | A |
| | | 25 | 9 | |
| | | 50 | 9 | |
| tamarind gum | Glyloid 6C from DSP Gokyo Food & Chemical Co., Ltd.. | 10 | 16 | B |
| | | 25 | 13 | |
| | | 50 | 6 | |
| glucomannan | Rheolex RS from Shimizu Chemical Corp. | 10 | 16 | B |
| | | 25 | 14 | |
| | | 50 | 8 | |
| guar gum | KT-0104 from DSP Gokyo Food & Chemical Co., Ltd.. | 10 | 10 | AA |
| | | 25 | 9 | |
| | | 50 | 10 | |
| alginic acid | Duck Acid from Kibun Food Chemifa Co., Ltd. | 10 | 59 | C |
| | | 25 | 35 | |
| | | 50 | 29 | |
| alginic acid | Snow Acid Algin G from Fuji Chemical Industry Co., Ltd. | 10 | 47 | C |
| | | 25 | 34 | |
| | | 50 | 27 | |
| ι (iota) type carrageenan | Gelcarin GP379NF from FMC | 10 | 23 | B |
| | | 25 | 15 | |
| | | 50 | 13 | |
| λ (lambda) type carrageenan | Viscarin GP209NF from FMC | 10 | 8 | AA |
| | | 25 | 7 | |
| | | 50 | 8 | |
| magnesium stearate | Taiyo Chemical Industry Co., Ltd. | 10 | 73 | B |
| | | 25 | 14 | |
| | | 50 | 3 | |

As shown in Table 2, it is clear that penetration of the acidic solution was very remarkably inhibited when using a gelling agent or a water repellent agent. When using only lactose (excipient) in the comparative example, the penetrance was 100% as is clear from Example 1. The results exhibited when using alginic acid were mediocre (an evaluation of "C").

As shown in Table 2, guar gum, λ (lambda) type carrageenan, and pectin (GENU Pectin DD slow set-J from Sansho Co., Ltd.) received a rank of AA. Xanthan gum and locust bean gum received a rank of A. Magnesium stearate, tamarind gum, glucomannan, and ι (iota) type carrageenan received a rank of B. Alginic acid received a rank of C.

Example 3

Mixed powders were prepared by mixing into lactose 10% and 25% by weight of the three powders that were evaluated as Rank AA in Example 2 (i.e., guar gum, λ

(lambda) type carrageenan, and pectin (GENU Pectin DD slow set-J from Sansho Co., Ltd.)), relative to the lactose. These mixed powders were filled into an acid-resistant hard capsule from Capsugel (DRCAPS™, Size 1, colorless and transparent). Similarly, mixed powders were prepared by mixing into lactose 10% by weight of the powder that was evaluated as Rank C in Example 2 (alginic acid). This mixed powder was filled into the same type of hard capsule. Further, a comparative example was prepared by filling only lactose into the same type of hard capsule.

These filled hard capsules prepared above were immersed for two hours in a pH 1.2 solution (Japanese Pharmacopeia, First Solution) colored with Blue No. 1 at 37° C. and subsequently removed. The hard capsules were then cut in half in the longitudinal axis direction with a sharp scalpel to expose a cross-section thereof. The hard capsules were examined to observe how the blue-colored acidic solution penetrated through the hard capsule outer shell into the capsule contents and the extent of penetration (or in other words, whether or not penetration was inhibited).

Figure 1:
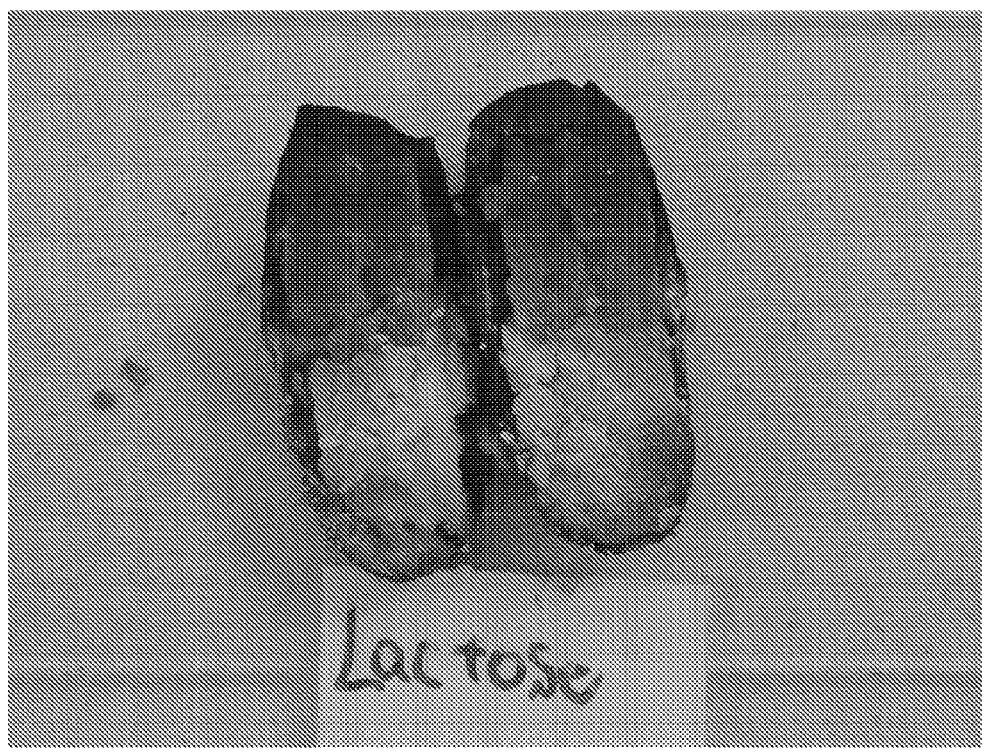
FIG. 1 is a photograph of a cross-section of a hard capsule filled with only lactose.
Figure 2A:
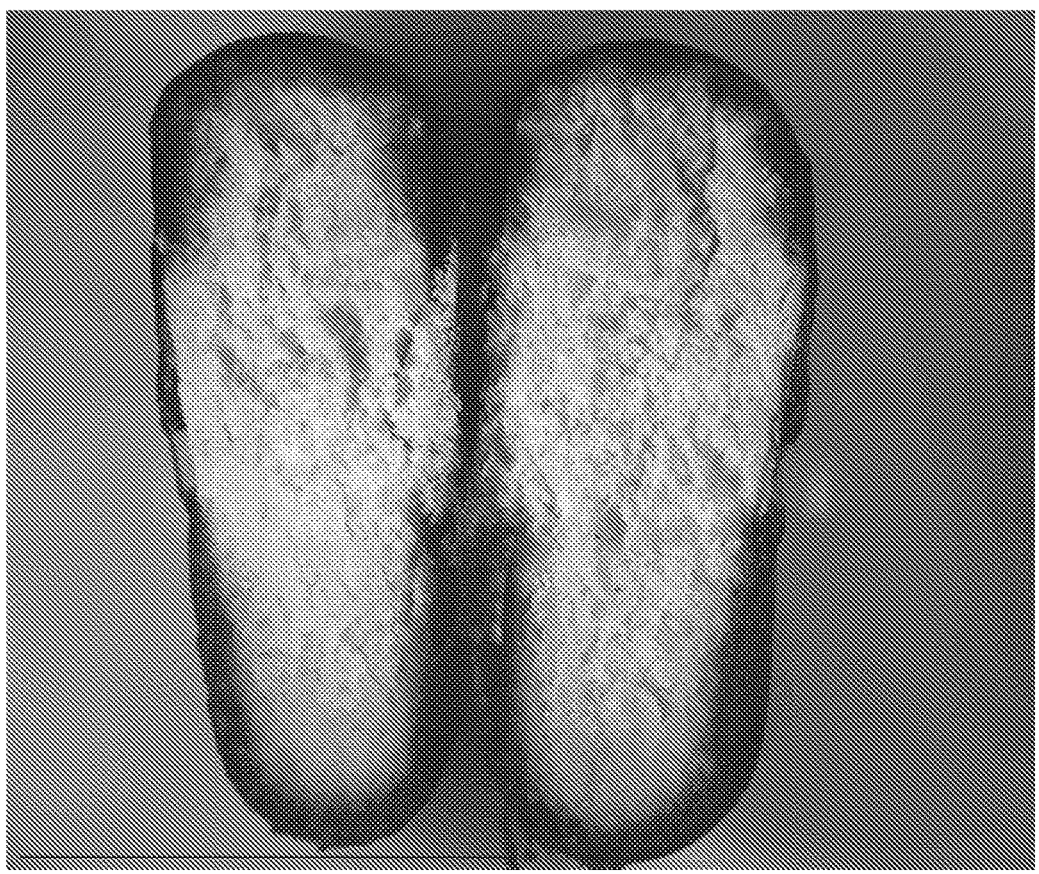
FIG. 2A is a photograph of a cross-section of a hard capsule filled with a mixed powder in which pectin ("GENU Pectin DD slow set-J" from Sansho Co., Ltd.) is mixed with lactose such that the pectin is 10% by weight relative to the lactose.
Figure 2B:
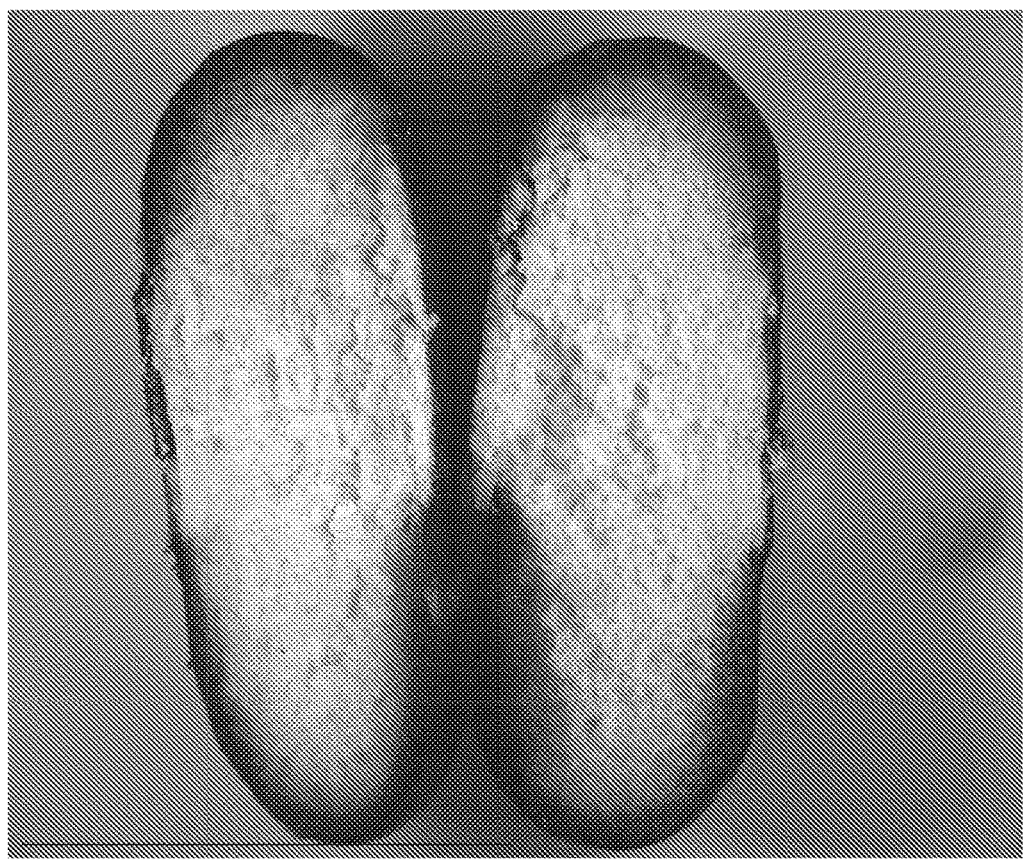
FIG. 2B is a photograph of a cross-section of a hard capsule filled with a mixed powder in which pectin ("GENU Pectin DD slow set-J" from Sansho Co., Ltd.) is mixed with lactose such that the pectin is 25% by weight relative to the lactose.
Figure 2C:
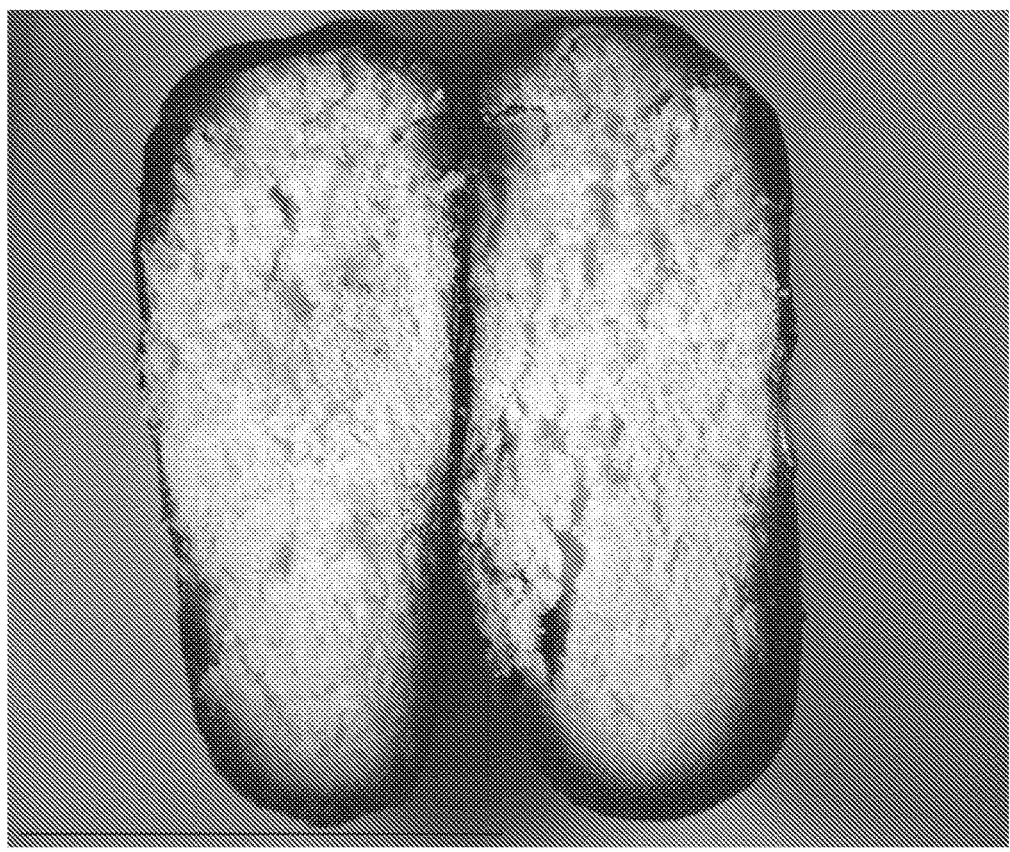
FIG. 2C is a photograph of a cross-section of a hard capsule filled with a mixed powder in which guar gum is mixed with lactose such that the guar gum is 10% by weight relative to the lactose.
Figure 2D:
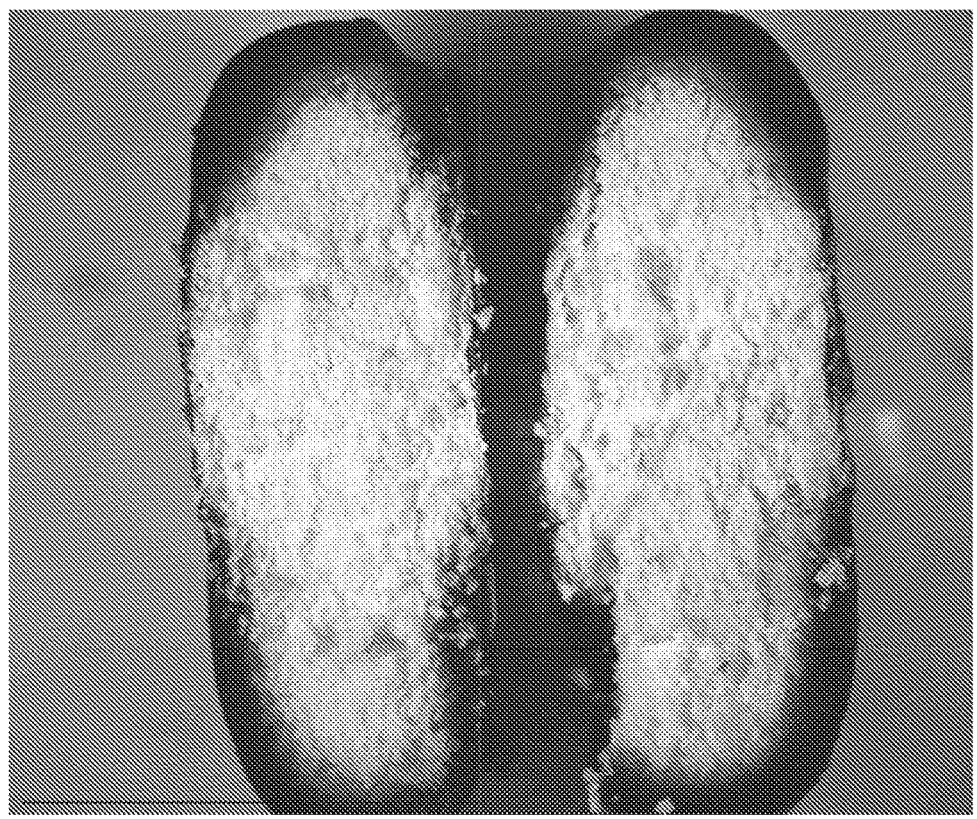
FIG. 2D is a photograph of a cross-section of a hard capsule filled with a mixed powder in which guar gum is mixed with lactose such that the guar gum is 25% by weight relative to the lactose.
Figure 2E:
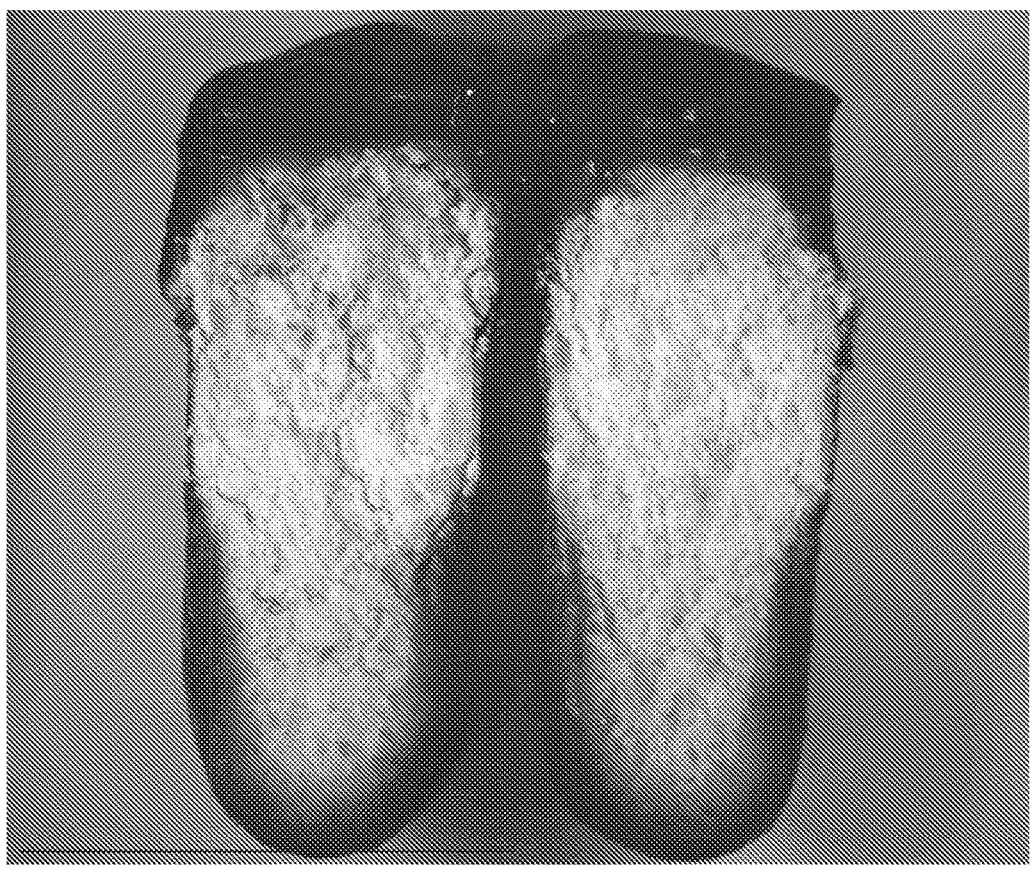
FIG. 2E is a photograph of a cross-section of a hard capsule filled with a mixed powder in which λ (lambda) type carrageenan is mixed with lactose such that the λ (lambda) type carrageenan is 10% by weight relative to the lactose.
Figure 2F:
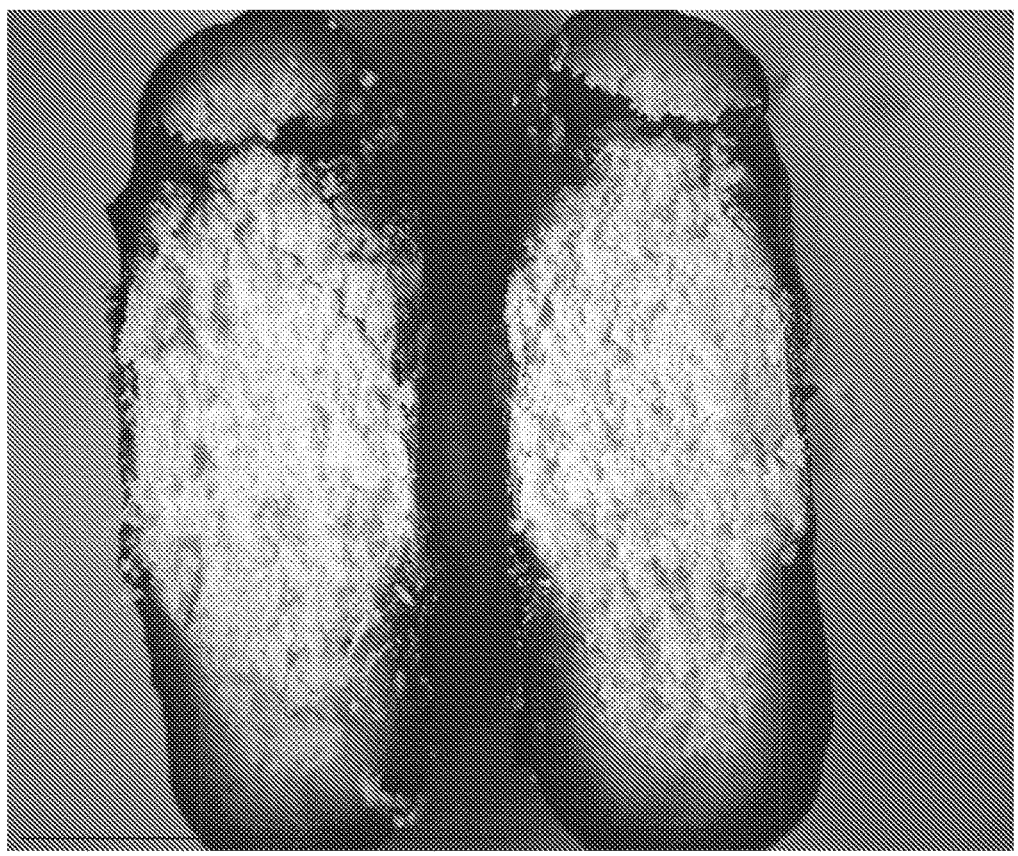
FIG. 2F is a photograph of a cross-section of a hard capsule filled with a mixed powder in which λ (lambda) type carrageenan is mixed with lactose such that the λ (lambda) type carrageenan is 25% by weight relative to the lactose.
Figure 3:
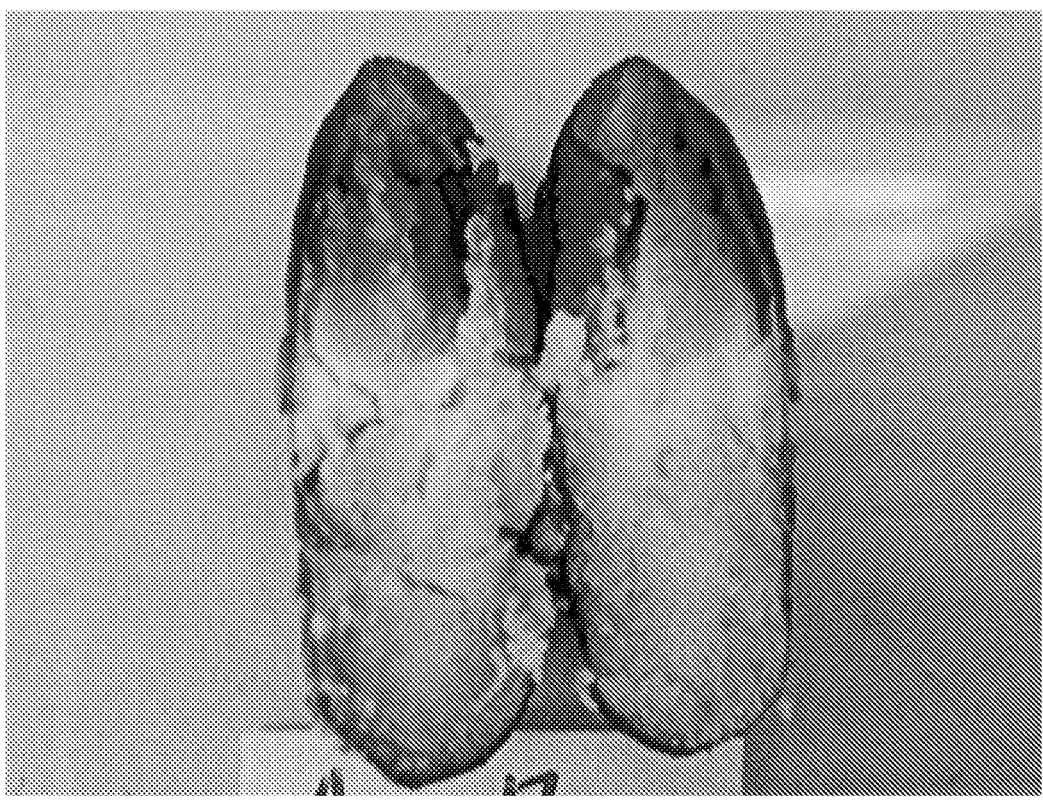
FIG. 3 is a photograph of a cross-section of a hard capsule filled with a mixed powder in which alginic acid is mixed with lactose such that the alginic acid is 10% by weight relative to the lactose.

Photographs of the cross-sections are shown in FIGS. 1, 2, and 3.

FIG. 1 is a photograph of a cross-section of a hard capsule filled with only lactose. As shown in this figure, when the hard capsule was filled with only lactose, the blue-colored acidic solution penetrated deep within the hard capsule, and extensive contact between the filled powder and the acidic solution occurred.

FIGS. 2A-2F show photographs of cross-sections of hard capsules filled with mixed powders in which guar gum, λ (lambda) type carrageenan, or pectin (GENU Pectin DD slow set-J from Sansho Co., Ltd.) is mixed with lactose such that the guar gum, λ (lambda) type carrageenan, or pectin is 10% or 25% by weight relative to the lactose. As shown in these figures, even when only 10% of these powders were included, the blue-colored acidic solution surprisingly penetrated only close to the shell of the hard capsules. Further, the majority of the interior of the hard capsules was dry, and contact between the filled powder and the acidic solution was largely blocked (inhibited).

FIG. 3 is a photograph of a cross-section of a hard capsule filled with a mixed powder in which alginic acid is mixed with lactose such that the alginic acid is 10% by weight relative to the lactose. In this case, contact between the filled powder and the acidic solution was blocked (inhibited) to some degree.

Example 4

Mixed powders were prepared by mixing into lactose 10% and 25% by weight of the three powders that were evaluated as Rank AA in Example 2 (i.e., guar gum, λ (lambda) type carrageenan, and pectin (GENU Pectin DD slow set-J from Sansho Co., Ltd.)), relative to the lactose. These mixed powders were filled into an acid-resistant hard capsule from Capsugel (DRCAPS™, Size 1, colorless and transparent). Further, a comparative example was prepared by filling only lactose into the same type of hard capsule.

These filled hard capsules prepared above were immersed for two hours in a pH 1.2 solution (Japanese Pharmacopeia, First Solution) at 37° C. (in contrast to Example 3, the solution was not colored with Blue No. 1) and subsequently removed. The hard capsules were then cut in half in the longitudinal axis direction with a sharp scalpel to expose a cross-section thereof.

One drop of a two-color coloration indicator called Bromophenol Blue (Bromophenol Blue: one type of acid base indicator used at a pH between 3.0 and 4.6; it becomes yellow when the pH of an aqueous solution is 3.0 or less, and it becomes blue-purple when the pH of an aqueous solution is 4.6 or more; this change is reversible) was dropped onto the exposed cross-section of each hard capsule.

In the results thereof, when the hard capsules were filled with the mixed powders prepared by mixing into lactose 10% and 25% by weight of the three powders that were evaluated as Rank AA in Example 2 (i.e., guar gum, λ (lambda) type carrageenan, and pectin (GENU Pectin DD slow set-J from Sansho Co., Ltd.)), relative to the lactose, the inside of the filled materials became blue-purple and thus the filled materials had a pH of 4.6 or more. Thus, it was understood that in these hard capsules, any influence by penetration of the acidic solution was effectively prevented. When the hard capsule was filled with only lactose as the comparative example, the inside of the filled materials became yellow, and thus influence by penetration of the acidic solution was apparent.

Example 5

Commercially available placenta (porcine or equine) was filled into size #1 acid resistant capsules from Capsugel (DRCAPS™) with either 100% placenta (porcine or equine), or 60 wt % placenta (porcine or equine) with 40 wt % gellan gum, banded, and submitted to acid resistance testing at pH 1.2, followed by dissolution testing at pH 6.8 (n=6). After two hours of the acid resistance test, the 100% placenta (porcine or equine) capsule lost titer due to degradation by the acid, and the filled powder was dissolved by the permeated acid through the shell. The cut capsule showed a dark brown gelled residue. In comparison, the 60 wt % placenta (porcine or equine) with 40 wt % gellan gum capsules showed 67% titer against the initial formulation, and the capsule interior after cutting open was intact. The 60 wt % placenta (porcine or equine) with 40 wt % gellan gum capsules disintegrated as expected within 8 minutes at pH 6.8.

Example 6

Commercially available Nattokinase (source *Bacillus subtilis* var.natto) dry enzyme powder was filled into size #2 acid resistant capsules from Capsugel (DRCAPS™) with either 100% dry powder enzyme, or 81 wt % dry powder enzyme powders with 9 wt % gellan gum and 9 wt % pH neutralizer (anhydrous tetrasodium pyrophosphate), banded, and submitted to acid resistance testing at pH 1.2, followed by dissolution testing at pH 6.8 (n=6). After two hours of the acid resistance test, the 100% dry enzyme powder was dissolved by the permeated acid through the shell. The cut capsule showed complete dissolution and damage of the dry powder enzyme. In comparison, the 81 wt % dry powder enzyme powders with 9 wt % gellan gum and 9 wt % pH neutralizer (anhydrous tetrasodium pyrophosphate) showed the capsule interior after cutting open the dry powder enzyme was visually intact. The 81 wt % dry powder enzyme powders with 9 wt % gellan gum and 9 wt % pH neutralizer (anhydrous tetrasodium pyrophosphate) disintegrated as expected within 12-24 minutes at pH 6.8.

I claim:
1. A hard capsule formulation comprising:
  a hydroxypropy methyl cellulose hard capsule with acid resistance, wherein said hard capsule is not treated with an enteric coating; and a fill composition in the hard capsule, the fill composition comprising an agent to inhibit invasion of gastric fluid into the fill composition and a pharmaceutical agent, wherein the agent to inhibit invasion of gastric fluid comprises a water repellent agent selected from calcium stearate, magnesium stearate, and carnauba wax and a gelling agent, the gelling agent comprising guar gum, pectin, ι (iota) type carrageenan, λ (lambda) type carrageenan, xanthan gum, locust bean gum, alginate, alginic acid, tamarind gum, glucomannan, agar, curdlan, gellan gum, or collagen.

2. The hard capsule formulation as claimed in claim 1, wherein said gelling agent is guar gum, λ (lambda) type carrageenan, xanthan gum, or locust bean gum.

3. The hard capsule formulation as claimed in claim 1, wherein said pharmaceutical agent is proteins, enzymes, or viable bacteria.

4. A method of inhibiting acid decomposition in a hydroxypropyl methyl cellulose hard capsule, comprising adding a water repellent agent to a fill composition in a hydroxypropyl methyl cellulose hard capsule, wherein the water repellent agent is calcium stearate, magnesium stearate, and carnauba wax and adding a gelling agent comprising guar gum, pectin, ι (iota) type carrageenan, λ (lambda) type carrageenan, xanthan gum, locust bean gum, alginate, alginic acid, tamarind gum, glucomannan, agar, curdlan, gellan gum, or collagen.

5. The method as claimed in claim 4, wherein the gelling agent comprises gellan gum.

6. The method as claimed in claim 4, wherein the fill composition further comprises a pharmaceutical agent, the pharmaceutical agent being proteins, enzymes, or viable bacteria.

7. The hard capsule formulation of claim 1, wherein water repellent agent comprises calcium stearate and the gelling agent comprises gellan gum.

* * * * *